United States Patent
Weigand et al.

(10) Patent No.: US 7,135,474 B2
(45) Date of Patent: *Nov. 14, 2006

(54) DERIVATIVES OF 2-(1-BENZYL-1H-PYRAZOLO(3,4-B) PYRIDINE-3-YL)-5(-4-PYRIDINYL)L-4-PYRIMIDINAMINES AND THE USE THEREOF AS QUANYLATE CYCLASE STIMULATORS

(75) Inventors: Stefan Weigand, Wuppertal (DE); Erwin Bischoff, Wuppertal (DE); Klaus Münter, Wülfrath (DE); Johannes-Peter Stasch, Solingen (DE); Elke Stahl, Bergisch Glasbach (DE)

(73) Assignee: Bayer Healthcare AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/514,909

(22) PCT Filed: May 5, 2003

(86) PCT No.: PCT/EP03/04668

§ 371 (c)(1),
(2), (4) Date: May 16, 2005

(87) PCT Pub. No.: WO03/097063

PCT Pub. Date: Nov. 27, 2003

(65) Prior Publication Data

US 2005/0222170 A1    Oct. 6, 2005

(30) Foreign Application Priority Data

May 17, 2002 (DE) ................ 102 22 550

(51) Int. Cl.
C07D 471/04 (2006.01)
A61K 31/505 (2006.01)
C07D 231/38 (2006.01)
(52) U.S. Cl. ...................... 514/256; 544/328
(58) Field of Classification Search ................ 544/328; 514/256
See application file for complete search history.

(56) References Cited

U.S. PATENT DOCUMENTS 6,693,102 B1 *  2/2004  Stasch et al. ............... 514/256

FOREIGN PATENT DOCUMENTS

| WO | 0006567  | 2/2000 |
| WO | 0006568  | 2/2000 |
| WO | 0006569  | 2/2000 |
| WO | 0242301  | 5/2002 |

OTHER PUBLICATIONS

Carvajal et al., Molecular Mechanism of cGMP-Mediated Smooth Muscle Relaxation, Journal of Cellular Physiology, 184:409-420, 2000.*
Yamashita et al., Mechanisms of Reduced Nitric Oxide/cGMP-Mediated Vasorelaxation in Transgenic Mice Overexpressing Endothelial Nitric Oxide Synthase, Hypertension, 36:97-102, 2000.*

* cited by examiner

Primary Examiner—Deepak Rao

(57) ABSTRACT

This application relates to compounds of the formula (I)

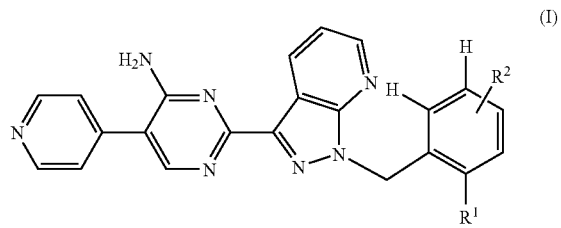

in which $R^1$ is chlorine, cyano, trifluoromethyl or methoxy and $R^2$ is hydrogen or flurorine; or $R^1$ and $R^2$ are both fluorine; and to pharmaceutically acceptable salts of these materials. Pharmaceutical compositions containing these materials, and methods of using them in treatment of hypertension and sexual dysfunction are also disclosed and claimed.

10 Claims, No Drawings

DERIVATIVES OF 2-(1-BENZYL-1H-PYRAZOLO(3,4-B)PYRIDINE-3-YL)-5(-4-PYRIDINYL)L-4-PYRIMIDINAMINES AND THE USE THEREOF AS QUANYLATE CYCLASE STIMULATORS

The present invention relates to chemical compounds which stimulate soluble guanylate cyclase, to the preparation thereof and to the use thereof as medicaments, in particular as medicaments for the treatment of cardiovascular disorders and/or sexual dysfunction.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyse the biosynthesis of cGMP from guanosine triposphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory site. The latter is of central importance for the mechanism of activation. NO is able to bind to the iron atom of heme and thus markedly increase the activity of the enzyme. Heme-free preparations cannot, by contrast, be stimulated by NO. CO is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological process, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation, endothelial dysfunction, atherosclerosis, angina pectoris, heart failure, thromboses, stroke, sexual dysfunction and myocardial infarction.

A possible way of treating such disorders which is independent of NO and aims at influencing the cGMP signal pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of haem. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole (YC-1, Wu et al., Blood 84 (1994), 4226; Mülsch et al., Brit. J. Pharmacol. 120 (1997), 681; fatty acids (Goldberg et al, J. Biol. Chem. 252 (1977), 1279; diphenyliodonium hexafluorophosphate (Pettibone et al., Eur. J. Pharmacol. 116 (1985), 307), isoliquiritigenin (Yu et al., Brit. J. Pharmacol. 114 (1995), 1587) and various substituted pyrazole derivatives (WO 98/16223).

In addition, WO 98/16507, WO 98/23619, WO 00/06567, WO 00/06568, WO 00/06569, WO 00/21954 WO 02/42299, WO 02/42300, WO 02/42301, WO 02/42302, WO 02/092596 and WO 03/004503 describe pyrazolopyridine derivatives as stimulators of soluble guanylate cyclase. Also described inter alia therein are pyrazolopyridines having a pyrimidine residue in position 3. Compounds of this type have very high in vitro activity in relation to stimulating soluble guanylate cyclase. However, it has emerged that these compounds have disadvantages in respect of their in vivo properties such as, for example, their behavior in the liver, their pharmacokinetic behavior, their dose-response relation or their metabolic pathway.

It was therefore the object of the present invention to provide further pyrazolopyridine derivatives which act as stimulators of soluble guanylate cyclase but do not have the disadvantages, detailed above, of the compounds from the prior art.

This object is achieved by the present invention through the compounds as claimed in claim 1. These novel pyrazolopyridine derivatives are distinguished by a 4-amino-5-(pyridin-4-yl)pyrimidine residue in position 3 and a substituted benzyl radical in position 1.

Specifically, the present invention relates to compounds of the formula (I)

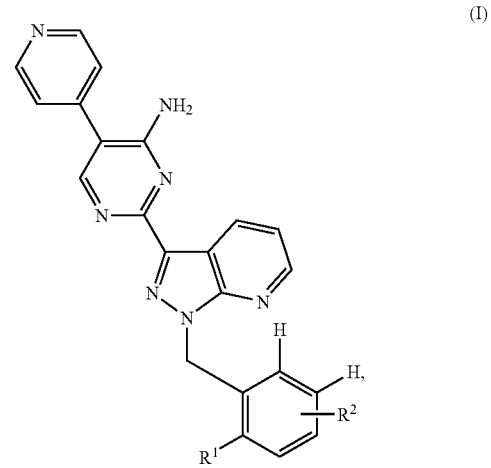

in which
R$^1$ is chlorine, cyano, trifluoromethyl or methoxy,
and
R$^2$ is hydrogen or fluorine,
or
R$^1$ is fluorine, and
R$^2$ is fluorine,
and salts, isomers and hydrates thereof.

The compounds according to the invention of the formula (I) may also be in the form of their salts. Mention may generally be made here of salts with organic or inorganic bases or acids.

Physiologically acceptable salts are preferred for the purposes of the present invention. Physiologically acceptable salts of the compound according to the invention may be salts of the substances according to the invention with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, p-toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts may likewise be metal or ammonium salts of the compound according to the invention having a free carboxyl group. Particularly preferred examples are sodium, potassium, magnesium or calcium salts, and ammonium salts derived from ammonia or organic amines such as, for example, ethylamine, di- or triethylamine, di- or triethanolamine, dicyclohexylamine, dimethylaminoethanol, arginine, lysine or ethylenediamine.

The compounds according to the invention may exist in tautomeric forms. This is known to the skilled person, and the invention likewise encompasses such forms.

The compounds according to the invention may furthermore be in the form of their possible hydrates.

A symbol * on a bond denotes the product of linkage in the molecule.

Preference is given to compounds of the formula (Ia)

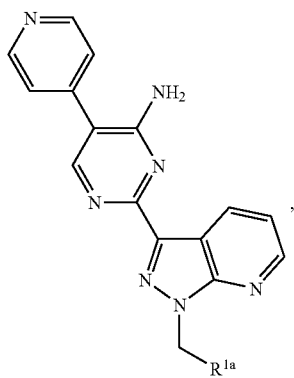

in which

R$^{1a}$ is selected from the group of

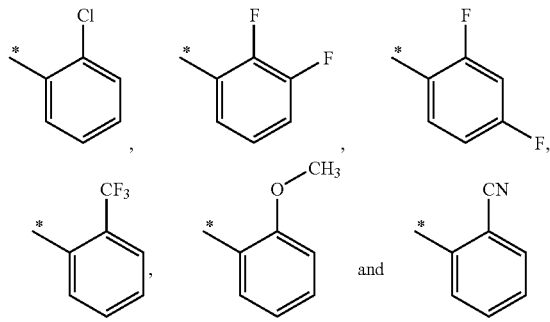

and salts, isomers and hydrates thereof.

Preference is given to the compound of the formula (Ia) in which

R$^{1a}$ is

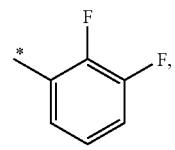

and salts, isomers and hydrates thereof.

The compounds according to the invention of the formula (I) can be prepared by customary reaction steps familiar to the skilled person, for example in analogy to the processes described for the synthesis of the exemplary embodiments.

The compounds according to the invention of the formula (I) show a valuable range of pharmacological effects which could not have been predicted.

The compounds according to the invention of the formula (I) bring about vasorelaxation and an inhibition of platelet aggregation and lead to a reduction in blood pressure and an increase in coronary blood flow. These effects are mediated by direct stimulation of soluble guanylate cyclase and an intracellular increase in cGMP. In addition, the compounds according to the invention of the formula (I) enhance the effect of substances which increase the cGMP level, such as, for example, EDRF (endothelium derived relaxing factor), NO donors, protoporphyrin IX, arachidonic acid or phenylhydrazine derivatives.

They can therefore be employed in medicaments for the treatment of cardiovascular disorders such as, for example, for the treatment of high blood pressure and heart failure, stable and unstable angina pectoris, peripheral and cardiac vascular disorders, of arrhythmias, for the treatment of thromboembolic disorders and ischemias such as myocardial infarction, stroke, transitory and ischemic attacks, disturbances of peripheral blood flow, prevention of restenoses as after thrombolysis therapies, percutaneous transluminal angioplasties (PTAs), percutaneous transluminal coronary angioplasties (PTCAs), bypass and for the treatment of arteriosclerosis, asthmatic disorders and diseases of the urogenital system such as, for example, prostate hypertrophy, erectile dysfunction, female sexual dysfunction, osteoporosis, glaucoma, pulmonary hypertension, gastroparesis and incontinence.

The compounds according to the invention of the formula (I) are also suitable for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory loss, vascular dementia, craniocerebral trauma, stroke, dementia occuring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis. They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds according to the invention of the formula (I) are furthermore also suitable for controlling cerebral blood flow and thus represent effective agents for controlling migraine.

The compounds according to the invention of the formula (I) are also suitable for the prophylaxis and control of the sequelae of cerebral infarctions such as stroke, cerebral ischemias and craniocerebral trauma. They can likewise be employed for controlling states of pain.

In addition, the compounds according to the invention of the formula (I) have an anti-inflammatory effect and can therefore be employed as anti-inflammatory agents.

Furthermore the present invention also encompasses the combination of at least one compound according to the invention of the formula (I) with one or more organic nitrates or NO donors.

Organic nitrates and NO donors for the purposes of the invention are generally substances which display their therapeutic effect via release of NO or NO species. Mention may be made by way of example and preferably of: sodium nitroprusside, nitroglycerine, isosorbide dinitrate, isosorbide mononitrate, molsidomine and SIN-1.

In addition, the present invention also encompasses the combination with one or more compounds which inhibit breakdown of cyclic guanosine monophosphate (cGMP). These are preferably inhibitors of phosphodiesterases 1, 2 and 5; nomenclature of Beavo and Reifsnyder (1990), TiPS 11 pp. 150 to 155. Particularly preferred in this connection are inhibitors of phosphodiesterase 5 (PDE V inhibitors), especially one of the compounds sildenafil (Viagra™, EP-A 0 463 756, WO 94/28902), vardenafil (WO 99/24433) or tadalafil (WO 95/19978). These inhibitors potentiate the effect of the compounds according to the invention, and the desired pharmacological effect is increased.

The present invention further relates to medicaments which comprise at least one compound according to the invention, preferably together with one or more pharmacologically acceptable excipients or carriers, and to the use thereof for the aforementioned purposes.

The active ingredient may have systemic and/or local effects. For this purpose, it can be administered in a suitable way such as, for example, oral, parenteral, pulmonary, nasal, sublingual, lingual, buccal, rectal, transdermal, conjunctival, topical or as implant.

The active ingredient can be administered in administration forms suitable for these administration routes.

Suitable for oral administration are known administration forms which deliver the active ingredient rapidly and/or in a modified manner, such as, for example, tablets (uncoated and coated tablets, e.g. tablets provided with enteric coatings or film-coated tablets), capsules, sugar-coated tablets, granules, pellets, powders, emulsions, suspensions, solutions and aerosols.

Parenteral administration can take place with avoidance of an absorption step (intravenous, intraarterial, intracardiac, intraspinal or intralumbar) or with inclusion of an absorption (intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates and sterile powders.

Suitable for the other routes of administration are, for example, pharmaceutical forms for inhalation (inter alia powder inhalers, nebulizers), nasal drops/solutions, sprays; tablets or capsules for lingual, sublingual or buccal administration, suppositories, preparations for the ears and eyes, vaginal capsules, aqueous suspensions (lotions, shaking mixtures), lipophilic suspensions, ointments, creams, milk, pastes, dusting powders or implants, such as, for example, stents.

The active ingredients can be converted in a manner known per se into the stated administration forms. This takes place with use of inert non-toxic, pharmaceutically suitable excipients. These include, inter alia, carriers (for example microcrystalline cellulose), solvents (for example liquid polyethylene glycols), emulsifiers (for example sodium dodecyl sulfate), dispersants (for example polyvinylpyrrolidone), synthetic and natural biopolymers (for example albumin), stabilizers (for example antioxidants such as ascorbic acid), colourings (for example inorganic pigments such as iron oxides) or masking flavours and/or odours. The active ingredient can, where appropriate, be present also in microencapsulated form in one or more of the carriers indicated above.

The therapeutically effective compound of the formula (I) should be present in the pharmaceutical preparations detailed above in a concentration of about 0.1 to 99.5, preferably of about 0.5 to 95, % by weight of the complete mixture.

The pharmaceutical preparations detailed above may, apart from the compound according to the invention of the formula (I) also contain other active pharmaceutical ingredients.

It has generally proved to be advantageous both in human and in veterinary medicine to administer the active ingredient according to the invention in total amounts of about 0.001 to about 50, preferably 0.001 to 10, mg/kg of body weight every 24 hours, where appropriate in the form of a plurality of single doses, to achieve the desired results. A single dose contains the active ingredient according to the invention preferably in amounts of about 0.001 to about 30, in particular 0.001 to 3, mg/kg of body weight.

The present invention is explained in more detail below by means of non-restrictive preferred examples. Unless indicated elsewhere, all quantitative data relate to percentages by weight. Solvent ratios, dilution ratios and concentration data for liquid/liquid solutions relate in each case to volume.

Biological Investigations

Vasorelaxant Effect In Vitro

Rabbits are stunned by a blow to the back of the neck and are exsanguinated. The aorta is removed, freed of adherent tissue and divided into rings 1.5 mm wide, which are put singly under tension in 5 ml organ baths containing carbogen-gassed Krebs-Henseleit solution at 37° C. with the following composition (mM): NaCl: 119; KCl: 4.8; $CaCl_2 \times 2$ $H_2O$; $MgSO_4 \times 7$ $H_2O$: 1.4; $KH_2PO_4$: 1.2; $NaHCO_3$: 25; glucose: 10. The force of contraction is detected with Statham UC2 cells, amplified and digitized via A/D converters (DAS-1802 HC, Keithley Instruments Munich) and recorded in parallel on chart recorders. A contraction is generated by adding phenylephrine to the bath cumulatively in increasing concentration. After several control cycles, the substance to be investigated is investigated in each further run in increasing dosage in each case, and the height of the contraction is compared with the height of the contraction reached in the last preceding run. The concentration necessary to reduce the height of the control value by 50% ($IC_{50}$)

is calculated from this. The standard application volume is 5 μl, and the DMSO content in the bath solution corresponds to 0.1%.

Rabbit Model

Adult male chinchilla rabbits weighing 3–5 kg are adapted to being kept singly for several days after delivery. They have free access to water and can take feed for two hours a day. The animals are kept in a 10/14-hour day/night rhythm (light on from 8.00 h), and the room temperature is 22–24° C.

Three to six animals are used in each treatment group and are weighed immediately before the start of the test. For the i.v. administration, the substances are dissolved in Transcutol (GATTEFOSSE GmbH) and diluted in the ratio 3/7 with a 20% strength Cremophor solution (Cremophor (BASF), water). A volume of 0.5 ml/kg is injected into the ear vein. Water-soluble substances are injected in 0.9% sodium chloride solution.

For oral administration, the test substances are dissolved in a 6:10:9.69 glycerol:water:polyethylene glycol mixture and administered by gavage in a volume of 1 ml/kg.

Under resting conditions, the rabbit penis is invisible in the pubic region and is completely covered by the penis skin. The erection is assessed by measuring the length of the protruding penis with a slide calliper. The measurement is carried out 5, 10, 15, 30, 45, 60 and 120 minutes after administration of the substance and, after oral administration, additionally after 3, 4, 5 and 6 hours. The animals are for this purpose removed from the cage each time, held firmly by the neck fur and the rear paws, turned on their backs and measured. Corresponding solvent controls are carried out. (Compare reference: E. Bischoff, K. Schneider, Int. J. of Impotence Res. 2001, 13, 230–235; E. Bischoff, U. Niewoehner, H. Haning, M. Es Sayed, T. Schenke, K. H. Schlemmer, The Journal of Urology, 2001, 165, 1316–1318; E. Bischoff, Int. J. Impotence Res. 2001, 13, 146–148).

Determination of Pharmacokinetic Parameters after Intravenous and Oral Administration The substance to be investigated is administered intravenously as solution to animals (e.g. mice, rats, dogs), and oral administration takes place as solution or suspension by gavage. After administration of the substance, blood is taken from the animals at fixed times and is heparinized, and then plasma is obtained therefrom by centrifugation. The substance is quantified analytically in the plasma by LC/MS/MS. The plasma concentration/time courses found in this way are used to calculate the pharmacokinetic parameters by means of a validated pharmacokinetic computer program.

Inhibition of Cytochrome P450 Enzymes

The potential for inhibition of P-450 isoenzymes which are important for metabolism is investigated automatically in a 96-well format. Two different assays are used for this.

In the assay based on the formation of fluorescent metabolites, recombinant enzymes (e.g. CYP1A2, 2C8, 2C9, 2C19, 2D6 or 3A4) and in general substrates containing fluorescein or coumarin partial structures are employed. In each case one substrate concentration and 8 concentrations of the potential inhibitor are used. After incubation with the particular recombinant CYP enzyme, a fluorescence reader is used to measure the extent of fluorescent metabolites compared with the control (without inhibitor), and an $IC_{50}$ is calculated [Anal. Biochem. 248, 188 (1997)].

In the 2nd assay, human liver microsomes are used as enzyme source, and the CYP isoform-selective substrates used are phenacetin (CYP1A2), diclofenac (CYP2C9), dextromethorphan (CYP2D6) and midazolam (CYP3A4). The formation of the particular metabolite is measured using LC-MS/MS. Assuming that inhibition is competitive, $K_i$ values are calculated from the reduction in metabolite formation compared with the control (1 substrate and 3 inhibitor concentrations).

Induction of Cytochrome P450 Enzymes in Human Liver Cell Cultures

To investigate the potential for side effects of the substances according to the invention in relation to induction of cytochrome P450 enzymes, primary human hepatocytes are cultured with a cell density of $2.5 \times 10^5$ cells between two layers of collagen in 24-well microtiter plates at 37° C. with 5% $CO_2$ for 8 days. The cell culture medium is changed each day.

After 48 hours in culture, the hepatocytes are treated with different concentrations of the test substances, comparing with the inducers rifampicin (RIF; 50 μM), omeprazole (OME; 100 μM) and phenobarbital (PB; 2 mM), in duplicate determination for 5 days. The final concentrations of the test substances are 0.01–10 μg/ml.

The inductive effect of the test substances on the cytochrome (CYP) P450 enzymes 1A2, 2B6, 2C19 and 3A4 is determined by adding the substrates 7-ethoxyresorufin (CYP1A2), [$^{14}$C]-S-mephenytoin (CYP2B6 and 2C19) and [$^{14}$C]-testosterone (CYP3A4) to the cell cultures on day 8. The inductive potential of the test substances is found from the activities, measured in this way, of CYP1A2, 2B6, 2C19 and 3A4 enzymes of treated cells compared with untreated cells.

Synthesis of Starting Compounds and Exemplary Embodiments

Abbreviations:
ACN acetonitrile
conc. concentrated
DCI direct chemical ionization (in MS)
DCM dichloromethane
DIEA N,N-diisopropylethylamine
DMAP dimethylaminopyridine
DMSO dimethyl sulfoxide
DMF N,N-dimethylformamide
EA ethyl acetate
EI electron impact ionization (in MS)
eq. equivalent
equiv. equivalent
ESI electrospray ionization (in MS)
H hour
HPLC high pressure, high performance liquid chromatography
LC-MS coupled liquid chromatography/mass spectroscopy
LDA lithium diisopropylamide
m.p. melting point
MS mass spectroscopy
NMR nuclear magnetic resonance spectroscopy
RP-HPLC reverse phase HPLC
RT room temperature
$R_t$ retention time (in HPLC)
sat. saturated
THF tetrahydrofuran
TLC thin layer chromatography LC/MS and HPLC Methods Method 1 (LCMS)
Instrument: Micromass Platform LCZ, HP1100; column: Symmetry C18, 50 mm×2.1 mm, 3.5 μm; Eluent A: water+

0.05% formic acid, Eluent B: acetonitrile+0.05% formic acid; Gradient: 0.0 min 90% A→4.0 min 10% A→6.0 min 10% A; oven: 40° C.; flow rate: 0.5 ml/min; UV detection: 208–400 nm.

Method 2 (LCMS)

Instrument: Waters Alliance 2790 LC; column: Symmetry C18, 50 mm×2.1, 3.5 µm; Eluent A: water+0.1% formic acid, Eluent B: acetonitrile+0.1% formic acid; Gradient: 0.0 min 5% B→5.0 min 10% B→6.0 min 10% B; Temperature: 50° C.; flow rate: 1.0 ml/min; UV detection: 210 nm.

Method 3 (HPLC)

Instrument: HP 1100 with DAD detection; column: Kromasil RP- 18, 60 mm×2 mm, 3.5 µm; Eluent: A=5 ml $HClO_4$/l $H_2O$, B=ACN; Gradient: 0 min 2% B, 0.5 min 2% B, 4.5 min 90% B, 6.5 min 90% B; flow rate: 0.75 ml/min; Temp.: 30° C.; detection UV 210 nm.

Preparative RP-HPLC

Column: YMC-Gel; Eluent: acetonitrile/water (Gradient); flow rate: 50 ml/min; Temp.: 25° C.; detection UV 210 nm.

Starting Compounds

EXAMPLE 1A 1-(2-Chlorobenzyl)hydrazine

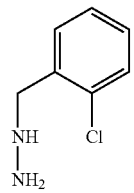

2.74 g (54.75 mmol) of hydrazine hydrate are introduced into 10 ml of methanol, and a solution of 3.00 g (14.60 mmol) of 2-chlorobenzyl bromide in 5 ml of methanol is added at RT. The temperature rises to 35–40° C. during this, and the mixture is then stirred at RT for 3 hours. The solvent is removed in vacuo, and the residue is taken up in 100 ml of diethyl ether, dried over magnesium sulfate and filtered off.

Total yield: 2.34 g (100% of theory) LC/MS (Method 2): $R_t$=0.37 min MS (EI): m/z=157 $(M+H)^+$ $^1$H-NMR (200 MHz, DMSO-$d_6$): δ=3.29–3.59 (s, 2H), 3.84 (s, 2H), 7.18–7.56 (m, 4H), 10.22 (br. s, 1H).

EXAMPLE 2A 1-(2,3-Difluorobenzyl)hydrazine

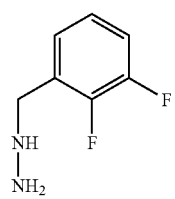

Preparation takes place in analogy to that described in Example 1A from 2.74 g (54.75 mmol) of hydrazine hydrate and 3.02 g (14.60 mmol) of 2,3-difluorobenzyl bromide. For work up, the residue is purified by flash chromatography (mobile phase: dichloromethane:methanol 30:1–10:1).

Total yield: 1.51 g (65% of theory) LC/MS (Method 2): $R_t$=0.32 min MS (EI): m/z=159 $(M+H)^+$ $^1$H-NMR (200 MHz, DMSO-$d_6$): δ=3.75–3.88 (m, 2H), 4.61–4.94 (br. s, 3H), 7.07–7.39 (m, 3H).

Preparation of the following compounds takes place in analogy to that described in Example 1 A:

| Example | Structure | Analytical data |
|---|---|---|
| 3A | ![structure] | HPLC (Method 3): $R_t$ = 3.28 min MS (EI): m/z = 191 $(M + H)^+$ $^1$H-NMR (300 MHz, $CDCl_3$): δ = 5.21 (s, 2H), 7.32–7.45 (m, 2H), 7.49–7.72 (m, 5H). |
| 4A | ![structure] | LC/MS (Method 2): $R_t$ = 0.32 min MS (EI): m/z = 159 $(M + H)^+$ $^1$H-NMR (300 MHz, DMSO-$d_6$): δ =3.69 (s, 2H), 6.93–7.33 (m, 4H), 7.40–7.56 (m, 2H). |
| 5A | ![structure] | LC/MS (Method 2): $R_t$ = 0.30 min MS (EI): m/z = 153 $(M + H)^+$ $^1$H-NMR (200 MHz, DMSO-$d_6$): δ = 3.65 (s, 3H), 6.85 (s, 2H), 6.84–7.03 (m, 3H), 7.15–7.36 (m, 3H), 7.43 (dd, 1H). |

EXAMPLE 6A

Sodium (1E)-1-cyano-3-ethoxy-3-oxo-1-propen-2-olate

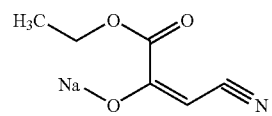

517 g (7.60 mol) of sodium methoxide are introduced into 3000 ml of diethyl ether and, while cooling in ice, 1121 g (7.60 mol) of diethyl oxalates are added over the course of 35 minutes. The mixture is stirred for 15 minutes and again cooled. 312 g (7.60 mol) of acetonitrile are added dropwise over the course of 20 minutes. The mixture is stirred at RT overnight, and the resulting crystals are filtered off with suction, washed with diethyl ether and dried.

Total yield: 1030 g (83% of theory) $^1$H-NMR (300 MHz, $CDCl_3$): δ=1.27 (t, 3H), 4.17 (q, 2H), 7.60 (s, 1H).

EXAMPLE 7A

Ethyl 5-amino-1-(2-chlorobenzyl)-1H-pyrazole-3-carboxylate

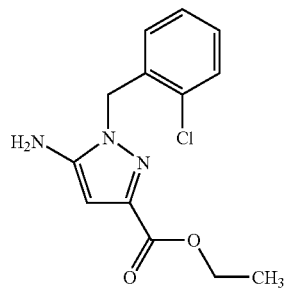

2.29 g (14.60 mmol) of 1-(2-chlorobenzyl)hydrazine from Example 1 A are dissolved in 60 ml of dioxane under argon. To this are added 2.38 g 814.60 mmol) of sodium (1E)-1-cyano-3-ethoxy-3-oxo-1-propen-2-olate from Example 6 A and 2.66 g (1.80 ml; 23.36 mmol) of trifluoroacetic acid. The mixture is boiled under reflux overnight and reacted further without further workup. LC/MS (Method 2): $R_t$=2.45 min MS (EI): m/z=280 (M+H)$^+$

EXAMPLE 8A

Ethyl 5-amino-1-(2,3-difluorobenzyl)-1H-pyrazole-3-carboxylate

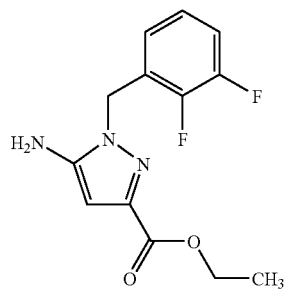

Preparation takes place in analogy to that described in Example 7 A from 1.50 g (9.48 mmol) of 1-(2,3-difluorobenzyl)hydrazine from Example 2 A, 1.55 g (9.48 mmol) of sodium (1E)-1-cyano-3-ethoxy-3-oxo-1-propen-2-olate from Example 6 A, 1.73 g (1.17 ml; 15.18 mmol) of trifluoroacetic acid and 40 ml of dioxane.

LC/MS (Method 1): $R_f$=3.90 min MS (EI): m/z=282 (M+H)$^{+1}$H-NMR (200 MHz, DMSO-d$_6$): δ=1.24 (t, 3H), 4.18 (q, 2H), 4.19–4.46 (br. s, 2H), 5.32 (s, 2H), 5.76 (s, 1H), 6.59–6.72 (m, 1H), 7.07–7.24 (m, 1H), 7.27–7.46 (m, 1H).

The preparation of the following compounds takes place in analogy to that described in Example 7A:

| Example | Structure | Analytical data |
|---|---|---|
| 9A | 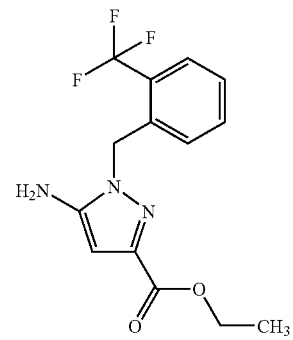 | LC/MS (Method 2): $R_t$ = 2.72 min MS (EI): m/z = 314 (M + H)$^+$ $^1$H-NMR (200 MHz, DMSO-d$_6$): δ = 1.14–1.42 (m, 3H), 4.12–4.26 (m, 2H), 5.40 (s, 2H), 7.42–7.88 (m, 7H). |
| 10A | 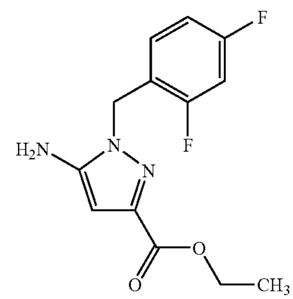 | LC/MS (Method 2): $R_t$ = 2.34 min MS (EI): m/z = 282 (M + H)$^+$ $^1$H-NMR (200 MHz, DMSO-d$_6$): δ = 1.16–1.36 (m, 3H), 4.10–4.30 (m, 2H), 5.22 (s, 2H), 6.85–7.15 (m, 4H), 7.21–7.37 (m, 2H). |
| 11A | 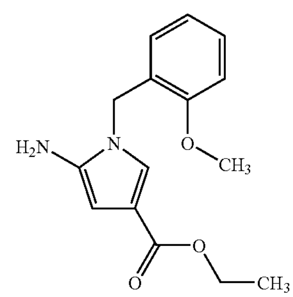 | LC/MS (Method 2): $R_t$ = 2.31 min MS (EI): m/z = 276 (M + H)$^+$ $^1$H-NMR (300 MHz, DMSO-d$_6$): δ = 1.20–1.33 (m, 3H), 3.65 (s, 3H), 4.15–4.29 (m, 2H), 5.11–5.16 (m, 2H), 6.78–7.07 (m, 5H), 7.16–7.33 (m, 2H). |

EXAMPLE 12A

Ethyl 1-(2-chlorobenzyl)-1H-pyrazole[3,4-b]pyridine-3-carboxylate

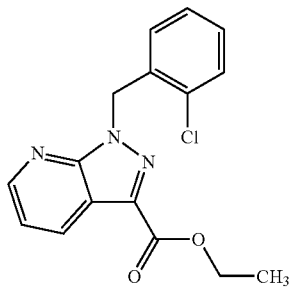

1.99 g (1.35 ml; 17.52 mmol) of trifluoroacetic acid and 1.45 g (14.60 mmol) of 3-dimethylaminoacroleine are added under argon to the solution of 4.08 g (14.60 mmol) of ethyl 5-amino-1-(2-chlorobenzyl)-1H-pyrazole-3-carboxylate from Example 7A. The mixture is boiled under reflux for 3 hours and worked up by removing the solvent in vacuo. The residue is purified by flash chromatography on silica gel (mobile phase: cyclohexane:ethyl acetate 7:1).

Total yield: 2.94 g (64% of theory) LC/MS (Method 1): $R_t$=4.74 min MS (EI): m/z=316 (M+H)$^{+1}$H-NMR (300 MHz, DMSO-d$_6$): δ=1.37 (t, 3H), 4.41 (q, 2H), 5.91 (s, 2H), 7.00–7.08 (m, 1H), 7.12–7.22 (m, 1H), 7.34–7.43 (m, 1H), 7.46–7.49 (m, 1H), 7.83 (d, 1H), 8.50 (dd, 1H), 8.71 (dd, 1H).

EXAMPLE 13A

Ethyl 1-(2,3-difluorobenzyl)-1H-pyrazole[3,4-b]pyridine-3-carboxylate

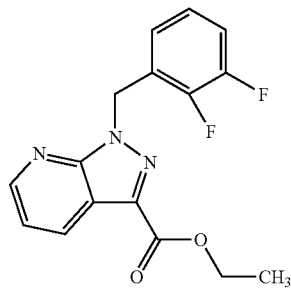

Preparation takes place in analogy to that described in Example 12 A from 4.11 g (14.60 mmol) of ethyl 5-amino-1-(2,3-difluorobenzyl)-1H-pyrazole-3-carboxylate from Example 8A, 1.99 g (1.35 ml; 17.52 mmol) of trifluoroacetic acid and 1.45 g (14.60 mmol) of 3-dimethylaminoacroleine.

Total yield: 1.94 g (29% of theory) LC/MS (Method 1): $R_t$=3.31 min MS (EI): m/z=318 (M+H)$^{+1}$H-NMR (300 MHz, DMSO-d$_6$): δ=1.37 (t, 3H), 4.41 (q, 2H), 5.91 (s, 2H), 7.00–7.08 (m, 1H), 7.11–7.22 (m, 1H), 7.33–7.45 (m, 1H), 7.49 (dd, 1H), 8.50 (dd, 1H), 8.71 (dd, 1H).

Preparation of the following compounds takes place in analogy to that described in Example 12 A:

| Example | Structure | Analytical data |
|---|---|---|
| 14A | | LC/MS (Method 2): $R_t$ = 3.62 min MS (EI): m/z = 350 (M + H)$^+$ |
| 15A | 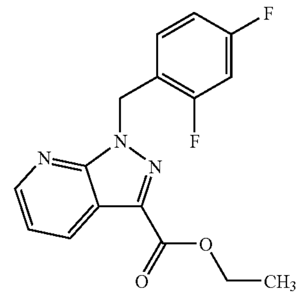 | LC/MS (Method 2): $R_t$ = 3.31 min MS(EI): m/z = 318 (M + H)$^+$ $^1$H-NMR (200 MHz, CDCl$_3$): δ = 1.48 (t, 3H), 4.53 (q, 2H), 5.85 (s, 2H), 6.67–6.92 (m, 2H), 7.04–7.21 (m, 1H), 7.26–7.37 (m, 1H), 8.53 (dd, 1H), 8.63 (dd, 1H). |
| 16A | 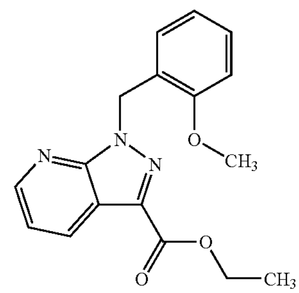 | LC/MS (Method 1): $R_t$ = 3.22 min MS (EI): m/z = 312 (M + H)$^+$ $^1$H-NMR (200 MHz, DMSO-d$_6$): δ = 1.37 (t, 3H), 3.78 (s, 3H), 4.40 (q, 2H), 5.77 (s, 2H), 6.69–6.89 (m, 2H), 6.98–7.09 (m, 1H), 7.29 (dt, 1H), 7.47 (dd, 1H), 8.50 (dd, 1H), 8.69 (dd, 1H). |

EXAMPLE 17A 1-(2-Chlorobenzyl)-1H-pyrazole[3,4-b]pyridine-3-carboxamide

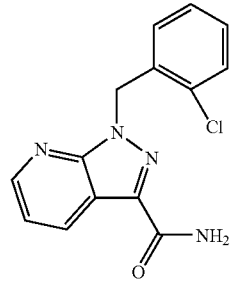

At room temperature, 2.94 g (9.31 mmol) of ethyl 1-(2-chlorobenzyl)-1H-pyrazole[3,4-b]pyridine-3-carboxylate from Example 12 A are suspended in 50 ml of 5.5 molar ammonia solution in methanol. The mixture is stirred at RT for 16 hours and evaporated to dryness again in a rotary evaporator. The residue is again mixed with 50 ml of ammonia solution and stirred at 50° C. for 3 hours. This is repeated over 3 days. After the last drying, the residue is taken up in 40 ml of diethyl ether, and the resulting crystals are filtered off with suction and dried. The mother liquor is again concentrated in a rotary evaporator and the mixture is again mixed with 50 ml of ammonia solution and stirred in an autoclave under autogenous pressure at 80° C. The residue is purified by flash chromatography on silica gel (mobile phase: cyclohexane:ethyl acetate 5:1).

Total yield: 1.33 g (50% of theory) LC/MS (Method 1): $R_t$=4.09 min $^1$H-NMR (300 MHz, DMSO-d$_6$): δ=5.85 (s, 2H), 6.87 (dd, 1H), 7.25 (dt, 1H), 7.34 (dt, 1H), 7.40 (dd, 1H), 7.51 (dd, 1H), 7.78 (br. s, 2H), 8.58 (dd, 1H), 8.64 (dd, 1H).

EXAMPLE 18A 1-(2,3-Difluorobenzyl)-1H-pyrazole[3,4-b]pyridine-3-carboxamide

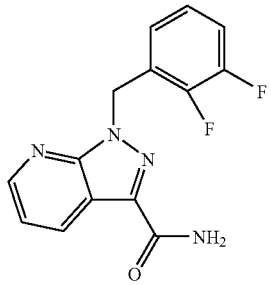

At room temperature, 1.90 g (5.99 mmol) of ethyl 1-(2,3-difluorobenzyl)-1H-pyrazole[3,4-b]pyridine-3-carboxylate from Example 13 A are suspended in 50 ml of 5.5 molar ammonia solution in methanol. The mixture is stirred at RT for 16 hours and then evaporated to dryness in a rotary evaporator. Dichloromethane is added and evaporated to dryness in a rotary evaporator twice more.

Total yield: 0.87 g (50% of theory) LC/MS (Method 1): $R_t$=4.00 min $^1$H-NMR (200 MHz, DMSO-d$_6$): δ=5.86 (s, 2H), 6.90–7.03 (m, 1H), 7.07–7.22 (m, 1H), 7.29–7.49 (m, 2H), 7.71 (d, 2H), 8.57 (dd, 1H), 8.66 (dd, 1H).

Preparation of the following compounds takes place in analogy to that described in Example 17 A:

| Example | Structure | Analytical data |
|---|---|---|
| 19A | | LC/MS (Method 1): $R_t$ = 4.36 min $^1$H-NMR (200 MHz, DMSO-d$_6$): δ = 5.96 (s, 2H), 6.66–6.81 (m, 1H), 7.42 (dd, 1H), 7.49–7.62 (m, 3H), 7.82 (dd, 2H), 8.55–8.74 (m, 2H). |
| 20A | 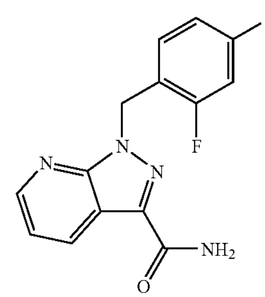 | LC/MS (Method 1): $R_t$ = 3.31 min $^1$H-NMR (200 MHz, DMSO-d$_6$): δ = 5.77 (s, 2H), 7.04 (dt, 1H), 7.20–7.45 (m, 3H), 7.56 (s, 1H), 7.82 (s, 1H), 8.56 (dd, 1H), 8.65 (dd, 1H). |
| 21A | 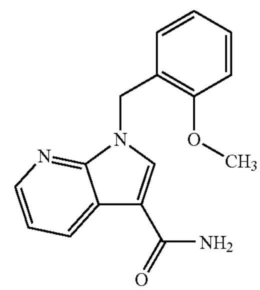 | LC/MS (Method 1): $R_t$ = 3.90 min MS (EI): m/z = 283 (M + H)$^+$ $^1$H-NMR (200 MHz, DMSO-d$_6$): δ = 3.83 (s, 3H), 5.73 (s, 2H), 6.61 (dd, 1H), 6.81 (dt, 1H), 7.04 (dd, 1H), 7.26 (dt, 1H), 7.38 (dd, 1H), 7.52 (s, 1H), 7.81 (s, 1H), 8.51–8.71 (m, 2H). |

EXAMPLE 22A 1-(2-Chlorobenzyl)-1H-pyrazole[3,4-b]pyridine-3-carbonitrile

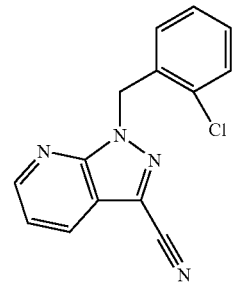

1.19 g (4.16 mmol) of 1-(2-chlorobenzyl)-1H-pyrazole[3,4-b]pyridine-3-carboxamide from Example 17 A are suspended in 30 ml of THF, and 0.84 g (0.86 ml; 10.66 mmol) of pyridine and 3.00 g (1.75 ml; 10.66 mmol) of trifluoroacetic anhydride are added. The mixture is stirred at room temperature overnight. The mixture is then poured into 300 ml of water and extracted three times with ethyl acetate. The combined organic phases are washed with saturated sodium bicarbonate solution and saturated sodium chloride solution, dried with magnesium sulfate and concentrated in a rotary evaporator.

Total yield: 0.880 g (79% of theory) LC/MS (Method 1): $R_t$=4.70 min MS (EI): m/z=269 (M+H)$^+$ $^1$H-NMR (200

MHz, DMSO-d$_6$): δ=5.92 (s, 2H), 7.18 (dd, 1H), 7.26–7.44 (m, 2H), 7.47–7.61 (m, 2H), 8.52 (dd, 1H), 8.80 (dd, 1H).

EXAMPLE 23A 1-(2,3-Difluorobenzyl)-1H-pyrazole[3,4-b]pyridine-3-carbonitrile

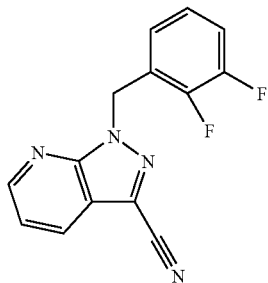

Preparation takes place in analogy to that described in Example 22 A with 0.84 g (2.91 mmol) of 1-(2,3-difluorobenzyl)-1H-pyrazole[3,4-b]pyridine-3-carboxamide from Example 18 A, 0.59 g (0.60 ml; 7.46 mmol) of pyridine and 2.10 g (1.22 ml; 7.46 mmol) of trifluoroacetic anhydride.

Total yield: 0.784 g (99% of theory) LC/MS (Method 2): R$_t$=3.22 min MS (EI): m/z=271 (M+H)$^+$ $^1$H-NMR (200 MHz, DMSO-d$_6$): δ=5.93 (s, 2H), 7.04–7.28 (m, 2H), 7.33–7.51 (m, 1H), 7.52–7.63 (m, 1H), 8.51 (dd, 1H), 8.81 (dd, 1H).

Preparation of the following compounds takes place in analogy to that described in Example 22 A:

| Example | Structure | Analytical data |
|---|---|---|
| 24A | 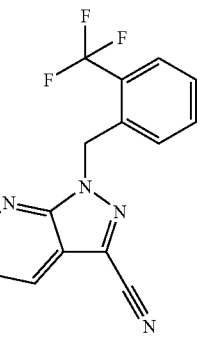 | LC/MS (Method 2): R$_t$ = 4.05 min<br>MS (EI): m/z = 303 (M + H)$^+$<br>$^1$H-NMR (MHz, 200): δ = 6.00 (s, 2H), 7.08 (d, 1H), 7.50–7.70 (m, 3H), 7.82 (d, 1H), 8.53 (dd, 1H), 8.78 (dd, 1H). |
| 25A | 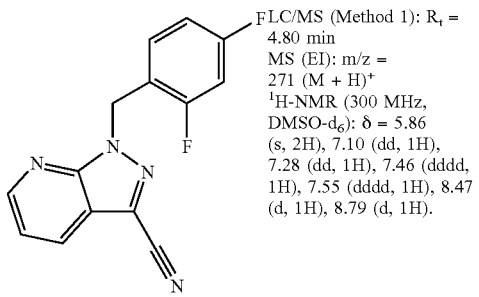 | LC/MS (Method 1): R$_t$ = 4.80 min<br>MS (EI): m/z = 271 (M + H)$^+$<br>$^1$H-NMR (300 MHz, DMSO-d$_6$): δ = 5.86 (s, 2H), 7.10 (dd, 1H), 7.28 (dd, 1H), 7.46 (dddd, 1H), 7.55 (dddd, 1H), 8.47 (d, 1H), 8.79 (d, 1H). |
| 26A | 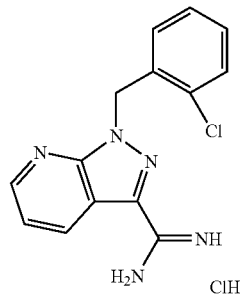 | LC/MS (Method 2): R$_t$ = 3.75 min<br>MS (EI): m/z = 265 (M + H)$^+$<br>$^1$H-NMR (200 MHz,): δ = 3.74 (s, 3H), 5.78 (s, 2H), 6.80–7.00 (m, 2H), 7.04 (d, 1H), 7.31 (ddd, 1H), 7.52 (dd, 1H), 8.50 (dd, 1H), 8.79 (dd, 1H). |

EXAMPLE 27A 1-(2-Chlorobenzyl)-1H-pyrazole[3,4-b]pyridine-3-carboximidamide hydrochloride 380 mg (1.41 mmol) from Example 22 A are suspended in 6 ml of methanol under argon. 45.84 mg (0.85 mmol) of sodium methoxide are added thereto, and the mixture is stirred at 50° C. for 5 hours. Then 189.12 mg (3.54 mmol) of ammonium chloride are added thereto, and the mixture is stirred under reflux for 2 hours. The reaction solution is concentrated in vacuo in a rotary evaporator, and the residue is suspended in 25 ml of saturated sodium carbonate solution and extracted three times with 75 ml of ethyl acetate each time. The combined organic phases are dried over magnesium sulfate, filtered and dried. The residue is taken up in 50 ml of diethyl ether and the product is precipitated with 4 normal hydrochloric acid in dioxane. The precipitate is filtered and dried under high vacuum.

Total yield: 0.200 g (44% of theory) LC/MS (Method 2): R$_t$=1.51 min MS (EI): m/z=286 (M+H−HCl$^+$) $^1$H-NMR (300 MHz, DMSO-d$_6$): δ=5.95 (s, 2H), 7.07 (dd, 1H), 7.29 (dt, 1H), 7.37 (dt, 1H), 7.49–7.59 (m, 2H), 8.58 (dd, 1H), 8.77 (dd, 1H), 9.42 (br. s, 4H).

EXAMPLE 28A 1-(2,3-Difluorobenzyl)-1H-pyrazole[3,4-b]pyridine-3-carboximidamide hydrochloride

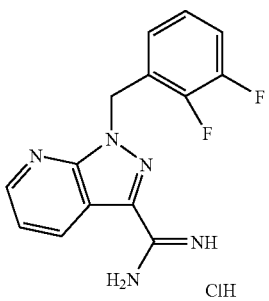

760 mg (2.81 mmol) from Example 23 A are suspended in 10 ml of methanol under argon. 30.4 mg (0.56 mmol) of sodium methoxide are added thereto, and the mixture is stirred at RT for 4 hours. Then 225.6 mg (4.22 mmol) of ammonium chloride are added thereto, and the mixture is stirred at RT for 5 hours. After addition of 20.5 mg of concentrated hydrochloric acid, the temperature is again reduced to RT and the product is freed of solvent in vacuo. The residue is suspended in 10% strength sodium carbonate solution and extracted three times with ethyl acetate. The combined organic phases are dried, filtered and dried. The residue is taken up in 15 ml of diethyl ether, and the product is precipitated with 1 molar hydrochloric acid in dioxane. The precipitate is filtered and dried under high vacuum.

Total yield: 0.775 g (76% of theory) LC/MS (Method 1): $R_t$=2.65 min MS (EI): m/z=288 (M+H)$^+$ $^1$H-NMR (300 MHz, DMSO-d$_6$): δ=5.94 (s, 2H), 7.08–7.24 (m, 1H), 7.34–7.47 (m, 1H), 7.54 (dd, 1H), 8.55 (dd, 1H), 8.78 (dd, 1H), 9.39 (br. s, 4H).

Preparation of the following compounds takes place in analogy to that described in Example 27 A:

| Example | Structure | Analytical data |
|---|---|---|
| 29A | | LC/MS (Method 2): $R_t$ = 2.45 min MS (EI): m/z = 320 (M + H)$^+$ $^1$H-NMR (MHz, 200, DMSO-d$_6$): δ = 6.02 (s, 2H), 6.95 (m$_c$, 1H), 7.48–7.66 (m, 3H), 7.81 (m$_c$, 1H), 8.60 (dd, 1H), 8.77 (dd, 1H), 9.2–9.6 (m, 3H). |
| 30A | 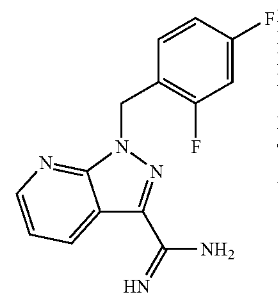 | LC/MS (Method 2): $R_t$ = 2.32 min MS (EI): m/z = 288 (M + H)$^+$ $^1$H-NMR (400 MHz, DMSO-d$_6$): δ = 5.84 (s, 2H), 7.04 (dd, 1H), 7.27 (dd, 1H), 7.39 (ddd, 1H), 7.49 (dd, 1H), 8.56 (d, 1H), 8.73 (d, 1H), 9.3 (br. S, 3H). |
| 31A | 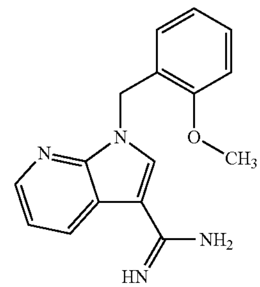 | LC/MS (Method 2): $R_t$ = 2.18 min MS (EI): m/z = 282 (M + H)$^+$ $^1$H-NMR (MHz, 200, DMSO-d$_6$): δ = 3.81 (s, 3H), 5.82 (s, 2H), 6.77–6.91 (m, 2H), 7.04 (d, 1H), 7.29 (m$_c$, 1H), 7.53 (dd, 1H), 8.56 (dd, 1H), 8.78 (dd, 1H), 9.3–9.6 (m, 3H). |

EXAMPLE 32A

4-[(Dimethylamino)methylene]pyridineacetonitrile (E/Z mixture)

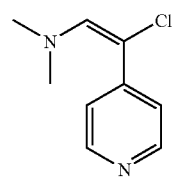

4-Pyridylacetonitrile 7.52 g (63.7 mmol) and tert-butoxy-bis(dimethylamino)methane 11.09 g (63.7 mmol) are stirred at 100° C. for 2 h. During this, liberated dimethylamine and t-butanol is discharged to the atmosphere by means of a vacuum pump through a gentle reduced pressure flow. Flash chromatography (dichloromethane/ethyl acetate 50:1->20:1) affords the title compound.

Yield: 10.2 g (93% of theory) R$_f$-Wert: 0.29 (dichloromethane/EA 20/1) $^1$H-NMR (300 MHz, DMSO-d$_6$): δ=3.25 (s, 6 H, 2×CH$_3$), 7.25 (d, 2 H, Ar—H), 7.80 (s, 1 H, Ar—H), 8.33 (d, 2 H, Ar—H). MS (ESI pos.): m/z=174 ([M+H]$^+$)

EXAMPLE 33A 1-(2-Fluorobenzyl)1H-pyrazolo[3,4-b]pyridine-3-carboxamidine

33 A-1 Ethyl 5-amino-1-(2-fluorobenzyl)pyrazole-3-carboxylate

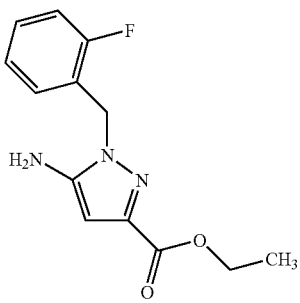

111.75 g (75 ml, 0.98 mol) of trifluoroacetic acid are added to 100 g (0.613 mol) of sodium salt of ethyl cyanopyruvate (prepared in analogy to Borsche and Manteuffel, Liebigs Ann. 1934, 512, 97) in 2.5 l of dioxane under argon with efficient stirring at room temperature, and the mixture is stirred for 10 minutes during which much of the precursor dissolves. Then 85.93 g (0.613 mol) of 2-fluorobenzylhydrazine are added, and the mixture is boiled overnight. After cooling, the crystals of sodium trifluoroacetate which have separated out are filtered off with suction and washed with dioxane, and the solution is reacted further as it is.

33 A-2 Ethyl 1-(2-fluorobenzyl)-1H-pyrazolo[3,4-b]pyridine-3-carboxylate

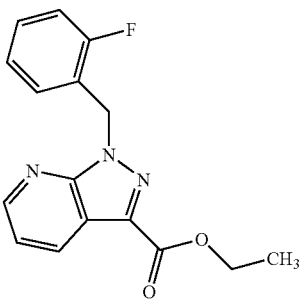

The solution obtained from Example 33 A-1 is mixed with 61.25 ml (60.77 g, 0.613 mol) of dimethylaminoacrolein and 56.28 ml (83.88 g, 0.736 mol) of trifluoroacetic acid and boiled under argon for 3 days. The solvent is then evaporated in vacuo, and the residue is added to 2 l of water and extracted three times with 1 l of ethyl acetate each time. The combined organic phases are dried with magnesium sulfate and concentrated in a rotary evaporator. Chromatography is carried out on 2.5 kg of silica gel, eluting with a toluene/ toluene-ethyl acetate=4:1 gradient. Yield: 91.6 g (50% of theory over two stages).

m.p. 85° C. $R_f$ (SiO$_2$, toluene/ethyl acetate 1:1): 0.83

33 A-3 1-(2-Fluorobenzyl)-1H-pyrazolo[3,4-b]pyridine-3-carboxamide

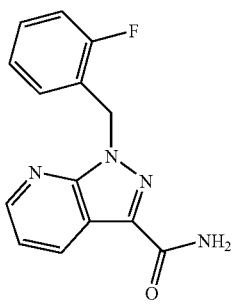

10.18 g (34 mmol) of the ester obtained in Example 33 A-2 are introduced into 150 ml of methanol which has been saturated with ammonia at 0–10° C. The mixture is stirred at room temperature for two days and then concentrated in vacuo. $R_f$ (SiO$_2$, toluene/ethyl acetate 1:1): 0.33

33 A-4 3-Cyano-1-(2-fluorobenzyl)-1H-pyrazolo[3,4-b]pyridine

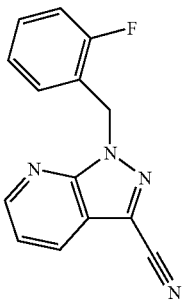

36.1 g (133 mmol) of 1-(2-fluorobenzyl)-1H-pyrazolo[3,4-b]pyridine-3-carboxamide from Example 33 A-3 are dissolved in 330 ml of THF, and 27 g (341 mmol) of pyridine are added. Then, over the course of 10 minutes, 47.76 ml (71.66 g, 341 mmol) of trifluoroacetic anhydride are added, during which the temperature rises to 40° C. The mixture is stirred at room temperature overnight. It is then added to 1 l of water and extracted three times with 0.5 l of ethyl acetate each time. The organic phase is washed with saturated sodium bicarbonate solution and with 1 N hydrochloric acid, dried with magnesium sulfate and concentrated in a rotary evaporator.

Yield: 33.7 g (100% of theory) m.p.: 81° C. $R_f$ (SiO$_2$, toluene/ethyl acetate 1:1): 0.74

33 A-5 Methyl (2-fluorobenzyl)-1H-pyrazolo[3,4-b]pyridine-3-carboximidate

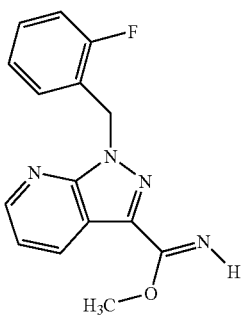

30.37 g (562 mmol) of sodium methoxide are dissolved in 1.5 l of methanol, and 36.45 g (144.5 mmol) of 3-cyano-1-(2-fluorobenzyl)-1H-pyrazolo[3,4-b]pyridine (from Example 33 A-4) are added. The mixture is stirred at room temperature for 2 hours and the resulting solution is employed directly for the next stage.

33 A-6 1-(2-Fluorobenzyl)-1H-pyrazolo[3,4-b]pyridine-3-carboximidamide

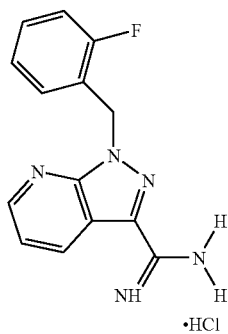

The solution of methyl (2-fluorobenzyl)-1H-pyrazolo[3,4-b]pyridine-3-carboximidate in methanol obtained from Example 33 A-5 is mixed with 33.76 g (32.19 ml, 562 mmol) of glacial acetic acid and 9.28 g (173 mmol) of ammonium chloride and stirred under reflux overnight. The solvent is evaporated in vacuo, the residue is thoroughly triturated with acetone, and the precipitated solid is filtered off with suction.

$^1$H-NMR (DMSO-$d_6$, 200 MHz): δ=5.93 (s, 2H); 7.1–7.5 (m, 4 H); 7.55 (dd, 1H); 8.12 (dd, 1H); 8.30 (dd, 1H); 9.5 (bs, 4H exchangeable) ppm. MS (EI): m/z=270.2 (M−HCl)

EXAMPLE 34A

2-[1-[(2-fluorophenyl)methyl]-1H-pyrazolo[3,4-b]pyridin-3-yl]-5-(4-pyridinyl)-4-pyrimidinamine

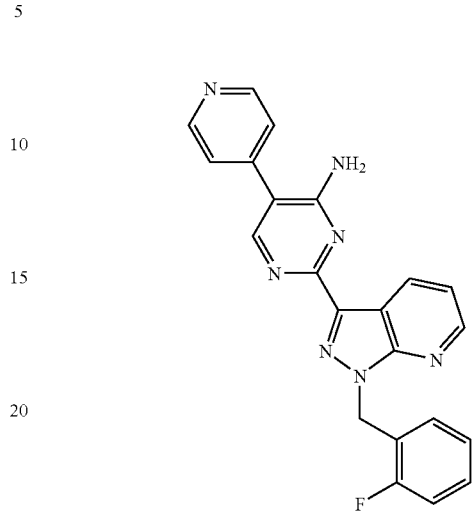

0.50 g (1.9 mmol) of 1-(2-fluorobenzyl)-1H-pyrazolo[3,4-b]pyridine-3-carboximidamide from Example 33 A and 4-[(dimethylamino)methylene]pyridineacetonitrile (0.32 g, 1.9 mmol) from Example 32 A are suspended in xylene, and BF$_3$*OEt$_2$ (71 μl, 79 mg, 0.56 mmol, 0.3 equiv.) is added. After 19 h at 140° C., the mixture is allowed to cool to room temperature and concentrated in vacuo. The title compound is purified by flash chromatography on silica gel (dichloromethane:methanol 20:1) and subsequent stirring in acetonitrile.

Yield: 0.24 g (33% of theory) R$_f$: 0.17 (EA/methanol 20:1) m.p.: 254° C. Retention time: R$_t$=2.7 min (column: Symmetry, C-18, 3.5 μm, 50×2.1 mm, flow rate 0.5 ml/min, 40° C., Gradient: water (+0.1% formic acid): acetonitrile (+0.1% formic acid) at 0 min: 90:10, at 7.5 min 10:90)) $^1$H-NMR (300 MHz, DMSO-$d_6$): δ=5.81 (s, 2H, CH$_2$), 7.0–7.6 (m, 9 H, Ar—H, NH$_2$), 8.64 (m$_c$, 3 H, Ar—H), 9.05 (d, 1 H, Ar—H) MS (ESI pos.): m/z=398 ([M+H]$^+$) MS (ESI neg.): m/z=396 ([M−H]$^+$)

EXAMPLE 35A 2-(1H-Pyrazolo[3,4-b]pyridin-3-yl)-5-(4-pyridinyl)-4-pyrimidinamine

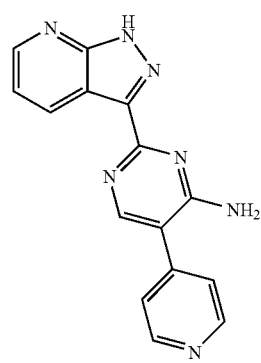

Approx. 15 ml of ammonia are condensed in a flask cooled with dry ice. 0.347 g (0.015 mol) of sodium is added thereto, and the mixture is stirred for 30 minutes. Then 1.50 g (0.004 mol) of the compound from Example 34 A are added thereto, and the mixture is stirred for 3 hours. 1.21 g (0.023 mol) of ammonium chloride are added to the mixture, and the remaining ammonia is evaporated off overnight through a scrubbing tower. For work up, water is added, and the crystals are filtered off with suction and dried. The residue is purified by column chromatography (mobile phase: dichloromethane:methanol 8:2) and then by RP-HPLC.

Total yield: 0.50 g (65% of theory) LC/MS (Method 2): $R_t$=1.09 min MS (EI): m/z=290 (M+H)$^{+1}$H-NMR (200 MHz, DMSO-$d_6$): δ=6.57 (br. s, 2H), 7.25 (dd, 1H), 7.52 (dd, 2H), 7.90 (s, 1H), 8.29 (s, 1H), 8.55 (dd, 1H), 8.70 (dd, 2H), 9.03 (dd, 1H).

Exemplary Embodiments

EXAMPLE 1

2-[1-(2-Chlorobenzyl)-1H-pyrazolo[3,4-b]pyridin-3-yl]-5-(4-pyridinyl)-4-pyrimidinamine

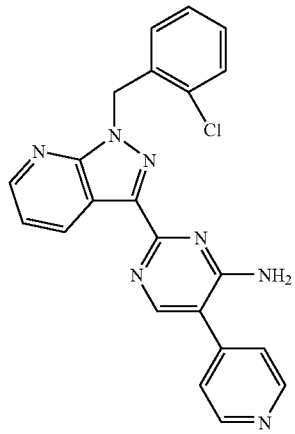

410 mg (1.27 mmol) of 1-(2-chlorobenzyl)-1H-pyrazole[3,4-b]pyridine-3-carboximidamide hydrochloride from Example 27 A and 242.46 mg (1.40 mmol) of 4-[(dimethylamino)methylene]pyridineacetonitrile from Example 32 A are suspended in a 3:1 benzyl alcohol:isobutanol mixture at RT. Then 25.75 mg (0.25 mmol) of triethylamine are added, and the mixture is stirred at 113° C. overnight. The solvent is then removed in vacuo, and the product is absorbed on silica gel. It is chromatographed (mobile phase: dichloromethane:methanol 30:1). The combined pure fractions are recombined and purified by preparative RP-HPLC.

Total yield: 70 mg (13% of theory) LC/MS (Method 1): $R_t$=3.52 min MS (EI): m/z=414 (M+H)$^{+1}$H-NMR (400 MHz, DMSO-$d_6$): δ=5.89 (s, 2H), 6.95 (d, 1H), 7.14 (br. s, 2H), 7.27 (t, 1H), 7.35 (t, 1H), 7.41 (dd, 1H), 7.50–7.58 (m, 3H), 8.28 (s, 1H), 8.61–8.73 (m, 3H), 9.07 (dd, 1H).

EXAMPLE 2

2-[1-(2,3-Difluorobenzyl)-1H-pyrazolo[3,4-b]pyridin-3-yl]-5-(4-pyridinyl)-4-pyrimidinamine

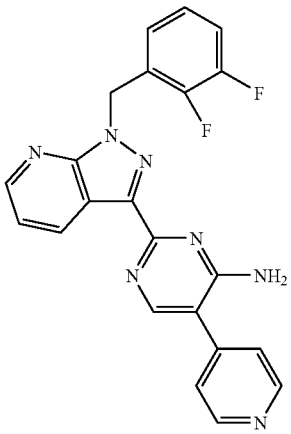

680 mg (1.88 mmol) of 1-(2,3-difluorobenzyl)-1H-pyrazolo[3,4-b]pyridine-3-carboximidamide hydrochloride from Example 28 A and 358 mg (2.07 mmol) of 4-[(dimethylamino)methylene]pyridineacetonitrile from Example 32 A are suspended in a 3:1 benzyl alcohol:isobutanol mixture at RT. Then 38.1 mg (0.38 mmol) of triethylamine are added, and the mixture is stirred at 87–90° C. overnight. A further 0.5 eq. of 4-[(dimethylamino)methylene]pyridineacetonitrile from Example 32 A is added, and the mixture is stirred at 87–90° C. for a further 6 hours. It is diluted with 3 ml of benzyl alcohol and 19 ml of isobutanol and briefly heated at 113° C. It is filtered hot, and the filtrate is slowly cooled while stirring. The solvent is then removed in vacuo, and the product is absorbed on silica gel. It is chromatographed (mobile phase: dichloromethane:methanol 30:1-20:1). The combined pure fractions are recombined and purified by preparative RP-HPLC.

Total yield: 180 mg (23% of theory) LC/MS (Method 1): $R_t$=3.24 min MS (EI): m/z=416 (M+H)$^{+1}$H-NMR (200 MHz, DMSO-$d_6$): δ=5.89 (s, 2H), 6.95–7.08 (m, 1H), 7.09–7.26 (m, 3H), 7.30–7.48 (m, 2H), 7.54 (dd, 2H), 8.28 (s, 1H), 8.61–8.73 (m, 3H), 9.05 (dd, 1H).

The following compounds are prepared in analogy to Example 1:

| Example | Structure | Analytical data |
|---|---|---|
| 3 | 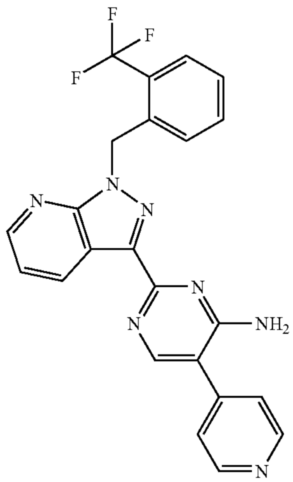 | LC/MS (Method 2): $R_t$ = 3.02 min<br>MS (EI): m/z = 448 (M + H)+<br>1H-NMR (300 MHz, DMSO-$d_6$):<br>δ = 5.99 (s, 2H), 6.80 (d, 1H), 7.1 (br. s, 2H), 7.41 (dd, 1H), 7.47–7.6 (m, 4H), 7.83 (dd, 1H), 8.30 (s, 1H), 8.6–8.7 (m, 3H), 9.08 (d, 1H). |
| 4 | 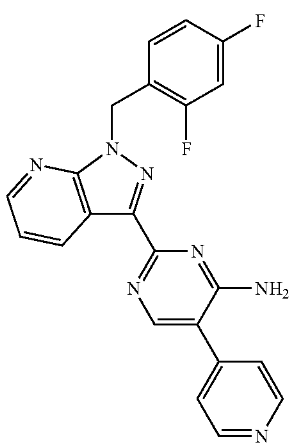 | LC/MS (Method 2): $R_t$ = 2.80 min $d_6$):<br>MS (EI): m/z = 416 (M + H)+<br>1H-NMR (300 MHz, DMSO-$d_6$):<br>δ = 5.32 (s, 2H), 7.0–7.2 (m, 3H), 7.2–7.45 (m, 3H), 7.54 (dd, 2H), 8.28 (s, 1H), 8.61–8.73 (m, 3H), 9.04 (dd, 1H). |
| 5 | 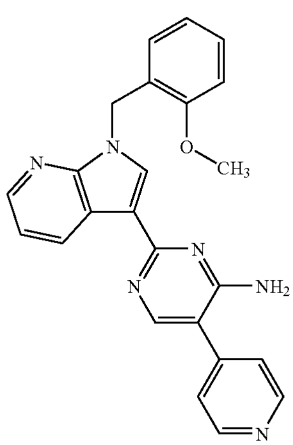 | LC/MS (Method 2): $R_t$ = 2.73 min<br>MS (EI): m/z = 410 (M + H)+<br>1H-NMR (300 MHz, DMSO-$d_6$):<br>δ = 5.75 (s, 2H), 6.22 (d, 1H), 6.82 (dd, 1H), 7.0–7.2 (m, 3H), 7.27 (dd, 1H), 7.38 (dd, 1H), 7.53 (d, 2H), 8.28 (s, 1H), 8.61 (dd, 1H), 8.69 (d, 2H), 9.04 (d, 1H). |

EXAMPLE 6

2-({3-[4-Amino-5-(4-pyridinyl)-2-pyrimidinyl]-1H-pyrazolo[3,4-b]pyridin-1-yl}-methyl)benzonitrile

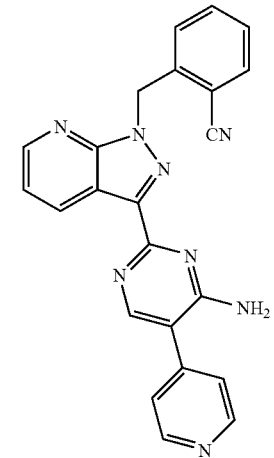

60 mg (0.21 mmol) of 2-(1H-pyrazolo[3,4-b]pyridin-3-yl)-5-(4-pyridinyl)-4-pyrimidinylamine from Example 35 A are suspended in 6 ml of dimethylformamide under argon. Addition of 26.38 mg (0.25 mmol) of sodium carbonate is followed by stirring at 50° C. for one hour. Then 40.66 mg (0.21 mmol) of 2-cyanobenzyl bromide are added thereto, and the mixture is stirred at 50° C. overnight. For work up, the mixture is filtered and the filtrate is adjusted to pH 4–5 with 1 normal hydrochloric acid and purified by preparative RP-HPLC.

Total yield: 40 mg (48% of theory) LC/MS (Method 2): $R_t$=1.84 min MS (EI): m/z=405 (M+H)+ 1H-NMR (300 MHz, DMSO-$d_6$): δ=5.99 (s, 2H), 6.69 (s, 1H), 7.02–7.17 (m, 2H), 7.22 (d, 1H), 7.41 (dd, 1H), 7.47–7.57 (m, 2H), 7.59–7.68 (m, 1H), 7.85–7.94 (m, 1H) 8.28 (s, 1H), 8.63–8.69 (m, 3H), 9.06 (dd, 1H).

The invention claimed is:

1. A compound of the formula (I)

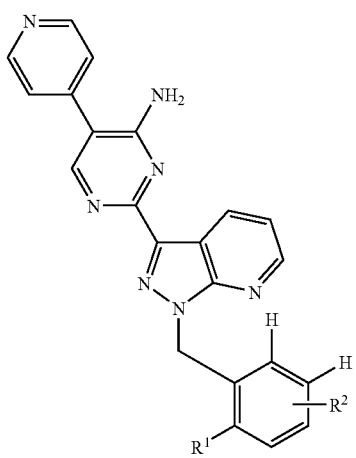

in which
R¹ is chlorine, cyano, trifluoromethyl or methoxy, and
R² is hydrogen or fluorine, or
R¹ is fluorine, and
R² is fluorine,
or a pharmaceutically acceptable salt thereof.

2. The compound of the formula (Ia) as claimed in claim 1

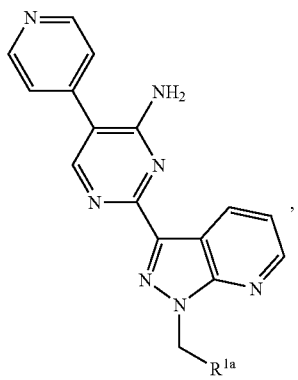
(Ia)

in which
R¹ᵃ is selected from the group consisting of

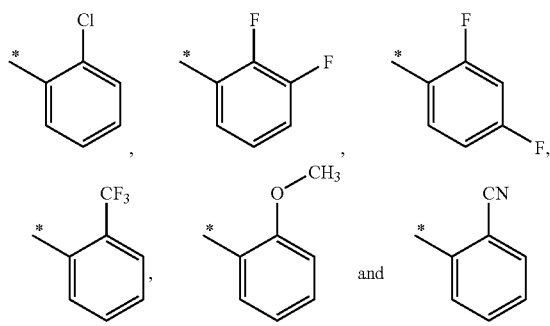

or a pharmaceutically acceptable salt thereof.

3. The compound of the formula (Ia) as claimed in claim 2, in which
R¹ᵃ is

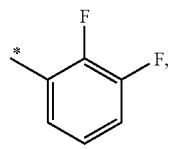

or a pharmaceutically acceptable salt thereof.

4. A pharmaceutical composition comprising at least one compound of the formula (I) as defined in claim 1, and at least one further excipient.

5. A pharmaceutical composition comprising at least one compound of the formula (I) as defined in claim 1 in combination with at least one organic nitrate or NO donor.

6. A pharmaceutical composition comprising at least one compound of the formula (I) as defined in claim 1 in combination with at least one compound which inhibits the breakdown of cyclic guanosine monophosphate (cGMP).

7. A method for the treatment of hypertension, comprising administering to a patient in need thereof a therapeutically effective amount of a compound of claim 1.

8. The method of claim 7, where compounds of the formula (I) as defined in claim 1 are employed in combination with at least one organic nitrate or NO donor or in combination with at least one compound which inhibits the breakdown of cyclic guanosine monophosphate (cGMP).

9. A method for the treatment of sexual dysfunction, comprising administering to a patient in need thereof a therapeutically effective amount of a compound of claim 1.

10. The method of claim 9, wherein the sexual dysfunction is erectile dysfunction or female sexual dysfunction.

* * * * *